United States Patent
Hartle et al.

(10) Patent No.: US 8,789,311 B2
(45) Date of Patent: Jul. 29, 2014

(54) MANUFACTURED SEED HAVING PACKING MATERIAL

(75) Inventors: Jeffrey E. Hartle, Tacoma, WA (US); William C. Carlson, Olympia, WA (US); Antony R. Shoaf, Lexington, NC (US)

(73) Assignee: Weyerhaeuser NR Company LLP, Federal Way, WA (US)

( * ) Notice: Subject to any disclaimer, the term of this patent is extended or adjusted under 35 U.S.C. 154(b) by 210 days.

(21) Appl. No.: 12/243,089

(22) Filed: Oct. 1, 2008

(65) Prior Publication Data
US 2009/0090050 A1    Apr. 9, 2009

Related U.S. Application Data

(60) Provisional application No. 60/977,172, filed on Oct. 3, 2007.

(51) Int. Cl.
*A01C 1/06* (2006.01)
*A01C 1/00* (2006.01)
*A01H 4/00* (2006.01)

(52) U.S. Cl.
CPC ........................... *A01H 4/006* (2013.01)
USPC ........................ 47/58.1 SE; 47/57.6

(58) Field of Classification Search
USPC .......................... 47/57.6, 58.1 SE
See application file for complete search history.

(56) References Cited

U.S. PATENT DOCUMENTS

| | | | |
|---|---|---|---|
| 2,671,985 A | | 3/1954 | Vogelsang |
| 4,353,183 A | * | 10/1982 | Estkowski ................... 47/56 |
| 4,769,945 A | * | 9/1988 | Motoyama et al. .......... 47/57.6 |
| 5,250,082 A | * | 10/1993 | Teng et al. ................... 47/57.6 |
| 5,799,439 A | * | 9/1998 | MacGregor .................. 47/57.6 |
| 6,119,395 A | * | 9/2000 | Hartle et al. ................. 47/57.6 |
| 7,356,965 B2 | * | 4/2008 | Carlson et al. .............. 47/57.6 |
| 2003/0167684 A1 | | 9/2003 | Carlson |
| 2005/0102895 A1 | * | 5/2005 | Bissonnette et al. ......... 47/57.6 |
| 2005/0108935 A1 | * | 5/2005 | Hirahara ..................... 47/57.6 |
| 2006/0032121 A1 | | 2/2006 | Hirahara |
| 2006/0064930 A1 | * | 3/2006 | Carlson et al. .............. 47/57.6 |
| 2007/0283621 A1 | | 12/2007 | Holloway |
| 2008/0155894 A1 | * | 7/2008 | Bissonnette et al. ......... 47/57.6 |
| 2008/0236037 A1 | * | 10/2008 | Rose et al. ................... 47/57.6 |
| 2009/0320360 A1 | * | 12/2009 | Starr et al. ................... 47/57.6 |

FOREIGN PATENT DOCUMENTS

EP    373348 A2    6/1990

\* cited by examiner

*Primary Examiner* — Kristen C Hayes
(74) *Attorney, Agent, or Firm* — Baker Hostetler LLP

(57) ABSTRACT

A manufactured seed is provided. The manufactured seed includes a seed shell housing a nutritive media and a restraint disposed within the seed shell. The restraint includes a cavity. The manufactured seed also includes an embryo disposed within the cavity and a fill material disposed within the cavity. The manufactured further includes a seal disposed on the seed shell to seal the embryo within the seed shell.

19 Claims, 1 Drawing Sheet

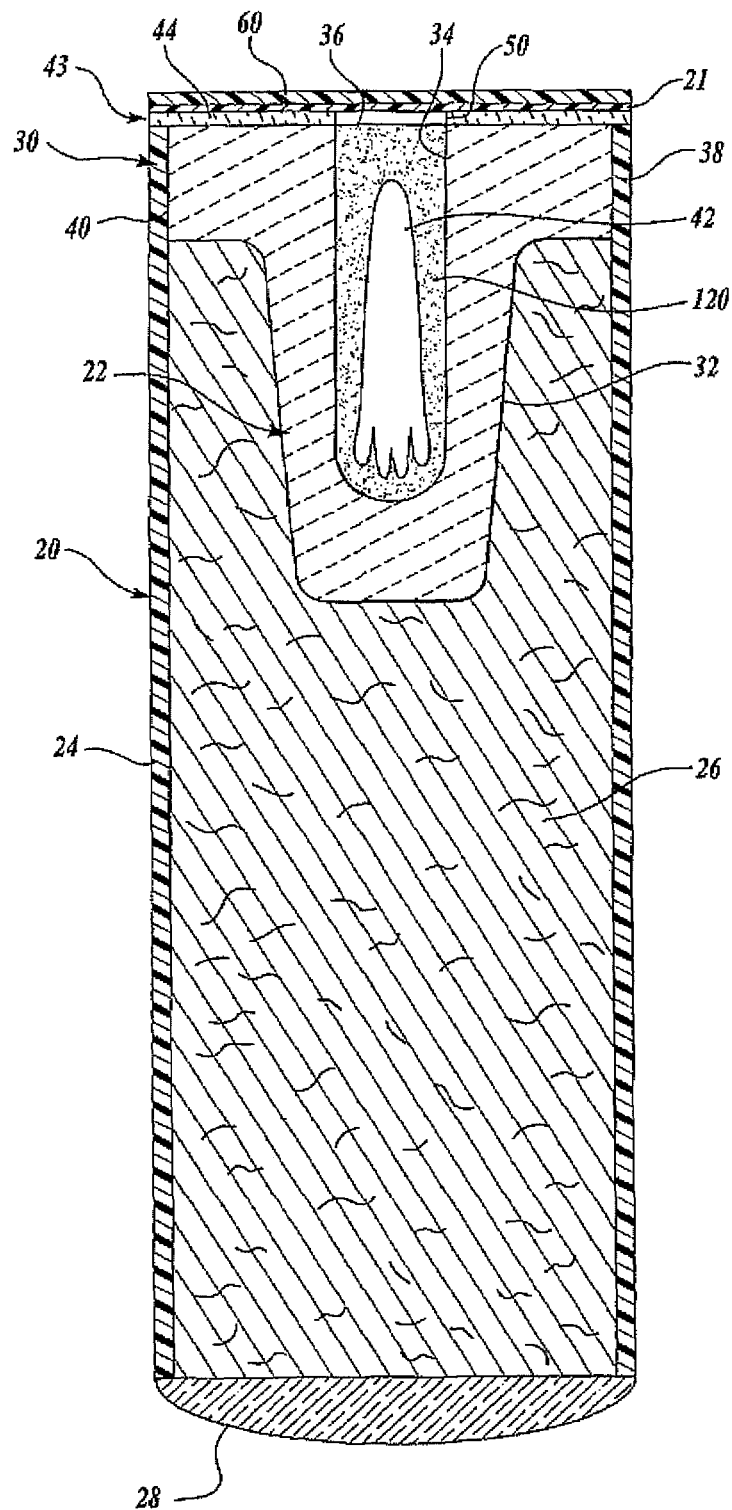

MANUFACTURED SEED HAVING PACKING MATERIAL

BACKGROUND

Asexual propagation of plants has been shown for some species to yield large numbers of genetically identical embryos, each having a capacity to develop into a normal plant. Such embryos are usually further cultured under laboratory conditions until they reach an autotrophic "seedling" state characterized by an ability to produce its own food via photosynthesis, resist desiccation, produce roots able to penetrate soil, and fend off soil microorganisms. Some researchers have experimented with the production of artificial seeds, known as manufactured seeds, in which individual plant somatic or zygotic embryos are encapsulated in a seed coat. Examples of such manufactured seeds are disclosed in U.S. Pat. No. 5,701,699, issued to Carlson et al., the disclosure of which is hereby expressly incorporated by reference.

Typical manufactured seeds include a seed shell, synthetic gametophyte and a plant embryo. A manufactured seed that does not include the plant embryo is known in the art as a "seed blank." The seed blank typically is a cylindrical capsule having a closed end and an open end. The synthetic gametophyte is placed within the seed shell to substantially fill the interior of the seed shell. A longitudinally extending hard porous insert, known as a cotyledon restraint, may be centrally located within one end of the seed shell, surrounded by the synthetic gametophyte, and includes a centrally located cavity extending partially through the length of the cotyledon restraint.

The cavity is sized to receive the plant embryo therein. The well-known plant embryo includes a radicle end and a cotyledon end. The plant embryo is deposited within the cavity of the cotyledon restraint, cotyledon end first. The plant embryo is then sealed within the seed blank by an end seat. There is a weakened spot in the end seal to allow the radicle end of the plant embryo to penetrate the end seal.

At has been discovered by the inventors of the present method that the rate of normal germination of an embryo from such manufactured seeds was unacceptably low. Their analysis noted that only about 30% of embryos within a study group of manufactured seeds produced a normal seedling having an expected root, cotyledons, etc. The present inventors observed that embryos, when inserted into the cavity of the cotyledon restraint having a diameter larger than the diameter of the embryo itself causes the cotyledons to be reflexed during somatic embryo development. This results in only the tips of the cotyledons to contact the walls of the cotyledon restraint cavity through which nutrition is passed from the gametophyte to the embryo. The present inventors theorize that this caused the unacceptably low productivity of the manufactured seeds.

Thus, there is a need for a method of preparing a material for use in a manufactured seed that improves the productivity of the manufactured seed.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A manufactured seed is provided. The manufactured seed includes a seed shell housing a nutritive media and a restraint disposed within the seed shell. The restraint includes a cavity. The manufactured seed also includes an embryo disposed within the cavity and a fill material disposed within the cavity. The manufactured further includes a seal disposed on the seed shell to seat the embryo within the seed shell.

DESCRIPTION OF THE DRAWINGS

The foregoing aspects and many of the attendant advantages of this invention will become better understood by reference to the following detailed description, when taken in conjunction with the accompanying drawings, wherein:

FIG. 1 is a side cross-sectional planar view of a manufactured seed having a packing material in accordance with certain aspects of the present disclosure.

DETAILED DESCRIPTION

A manufactured seed 20 having a fill material 120 constructed in accordance with certain aspects of the present disclosure may be best understood by referring to FIG. 1. The manufactured seed 20 includes a cylcap 22, a seed shell 24, nutritive media 26, such as a gametophyte, and a dead end seal 28. The seed shell 24 is suitably formed from a section of tubular material. In one embodiment, the seed shell 24 is a sectioned straw of fibrous material, such as paper. The sections of straw may be pretreated in a suitable coating material, such as wax.

In other embodiments, the seed shell 24 is formed from a tubular section of to biodegradable, plastic material. One such material is a utilized polylatic acid ("PLA") and is sold by MAT-UR of Los Angeles, Calif. Another material within the scope of the disclosure is a polycaprolactone ("PCL") mixture, such as Dow Tone P-787 (Dow Chemical Co., Midland, Mich. 48647) with a 1% Tegomer H SI6440 plasticizer (Degussa Goldschmidt Chemical Corp, 914 East Randolph Road, Hopewell, Va. 23860).

Such biodegradable plastic tubes are sectioned into appropriate lengths for a manufactured seed. Further, such biodegradable plastic tubes may or may not require a wax coating as such tubes are already resistive to environmental elements. It should be apparent that although sectioning tubes is preferred, other embodiments, such as obtaining tubes of appropriate size for use as manufactured seeds, are also within the scope of the present disclosure.

The cylcap 22, also known as a restraint, is suitably manufactured from a porous material having a hardness strong enough to resist puncture or fracture by a germinating embryo, such as a ceramic or porcelain material, and includes an end seal portion 30 and a cotyledon restraint portion 32. The cotyledon restraint portion 32 is suitably integrally or unitarily formed with the end seal portion 30. The cylcap 22 also includes a longitudinally extending cavity 34 extending through the end seal portion 30 and partially through one end of cotyledon restraint portion 32. The open end of the cavity 34 is known as a cotyledon restraint opening 36. The cavity 34 is sized to receive a plant embryo 42 therein.

In certain embodiments, as the cylcap 22 is suitably manufactured from a porous material, it may be desirable to coat the cylcap 22 with a barrier material to reduce the rate of water loss and restrict or reduce microbial entry. Such barriers include wax, polyurethane, glaze, nail polish, and a coating sold by H.B. Fuller of Minneapolis, Minn. under the product name PD124.

The end seal portion 30 is suitably circular when viewed in a top planar view and includes sidewalls 38. Although circular is the preferred embodiment of the end seal portion 30, other embodiments and shapes, such as polygonal, square, triangular, oval and other shapes, are also within the scope of the present disclosure.

In the embodiment of FIG. 1, the sidewalls 38 are defined by the thickness of the end seal portion 30 and has a diameter substantially equal to the inside diameter of the seed shell 24. In certain embodiments, the cylcap 22 is bonded to the seed shell 24 by heat. As a non-limiting example, during manufacturing, the cylcap 22 may be heated to a predetermined temperature, such that when the seed shell 24 and the cylcap 22 are co-joined, heat transferred between the cylcap 22 and the seed shell 24 causes either the seed shell 24, the cylcap 22, or both to melt, thereby bonding the two together. In other embodiments, the cylcap 22 and the primary end seal 44 are first heat welded, then in a separate step the combined primary end seal-cylcap is reheated and the seed shell 24 is also heated and the two are joined. Other methods of bonding the cylcap 22 to the seed shell 24, such as a wax bond or a hot glue melt, are also within the scope of the present disclosure.

The sidewalls 38 may include a tapered portion 40. The tapered portion 40 may be a chamfer of one end of the end seal portion 30. The tapered portion 40 assists in assembling the cylcap 22 to the seed coat 24 during manufacturing. Although a tapered portion 40 is preferred, other embodiments, such as a cylcap that does not include a tapered portion, are also within the scope of the present disclosure. An embryo 42 is disposed within the cavity 34 and is suitably sealed therein by a live end seal 43.

The live end seal 43 includes a primary end seal 44 and a secondary end seal 21. The primary end seal 44 is suitably formed from a PCL material described above and includes a centrally located opening 50. The opening 50 is sized to correspond to diameter of the cavity 34 of the cylcap 22 to permit a germinating embryo 42 to pass therethrough. The primary end seal 44 is suitably attached to the end seal portion 30 by a variety of methods, including glue or heat bonding.

As a non-limiting example, the primary end seal 44 is mated to a pre-heated cylcap 22, such that the opening 50 is located above the cavity 34. The heat welds or bonds the primary end seal 44 to the cylcap 22. It should be apparent that the primary end seal 44 may be attached to the cylcap 22 before or after the cylcap 22 is attached to the seed shell 24. Also, if the seed shell 24 is constructed from PCL, it is desirable but not necessary that the melt temperature of the primary end seal 44 and the seed shell 24 be similar.

As another non-limiting example of attaching the primary end seal 44 to the cylcap 22, includes an adhesive gasket. In this example, the primary end seal 44 is heat sealed or bonded to the cylcap 22 with the opening 50 co-axially aligned with the cavity 34. In this process, a form is used to bend edges of the primary end seal 44 around the perimeter of the end seal portion 30 of the cylcap 22. If the melt temperature of the primary end seal 44 and the seed shell 24 are different, then a low bloom cyanoacrylate is used as an adhesive gasket to bond the primary end seal 44 and the seed shell 22.

Heat is applied after the glue and is done so as to thin the glue seal by melting incongruities that typically occur when manufacturing the seed shell 24 and forming the adhesive joint. Thereafter, the cylcap 22, including the primary end seal 44, is attached to the seed shell 24. As noted above, this method is also suitable to a cylcap 22 that is already attached to the seed shell 24. Finally, the foregoing method of attaching a primary end seal 44 to a seed shell 24 may be used for heat weld compatible or incompatible materials.

The secondary end seal 21 will now be described in greater detail. In that regard, the secondary end seal 21 is suitably formed from a well-known sealing material, such as Parafilm®. The secondary end seal 21 is formed and attached to the primary end seal 44 by a well-known method, such as heat bonding or gluing. In some embodiments, a sealing wax may be used to facilitate bonding between the PCL and the Parafilm. The secondary end seal 21 also includes a predetermined burst strength to permit a germinating embryo 42 to penetrate through the live end seal 44.

Still referring to FIG. 1, the tertiary seal 60 will now be described in greater detail. The tertiary seal 60 and live end seal 43, as used in the present embodiment, define an outer sealing layer and an inner sealing layer, respectively. Although the live end seal 43 has been described as including both a primary end seal 44 and a second end seal 21, it should be apparent that the disclosure is not intended to be so limited. As a non-limiting example, the live end seal 43 may include only the secondary end seal 21 and, therefore, such embodiments are also within the scope of the present disclosure.

The combination of the tertiary seal 60 and live end seal 43 creates a sealing surface, wherein the sealing layer, defined by the tertiary seal 60, is made from a predetermined material that degrades in structural integrity after a predetermined exposure to environmental conditions. The tertiary seal 60 also serves as an anti-microbial sealant to seal and protect around the embryo as the embryo germinates and emerges from within the seed shell 24 and protects the cotyledon restraint cavity. Suitable materials used to manufacture the tertiary seal 60 include water soluble materials, wax, environmentally degradable materials, and biodegradable materials. Thus, such materials, as well as materials equivalent in structure and properties, are within the scope of the present disclosure.

As noted above, the seed shell 24 and primary end seal 44 are suitably formed from a polyester material, such as biodegradable plastic. One method of preparing the material for use in making components, such as the seed shell 24 and primary end seal 44, of the manufactured seed 20 in accordance with the present disclosure includes obtaining strips of material, such as strips of plastic. Such plastics within the scope of the appended claims includes biodegradable plastics, such as PCL.

The strips of material are annealed using well-known annealing methods to improve dimensional stability. In one non-limiting example, strips of PCL are annealed at a temperature of about 63° C. for a range of time substantially between 35 minutes and 90 minutes. In one embodiment, the strips of PCL are annealed for 45 minutes. The annealing time is a time sufficient to render the strips of PCL dimensionally stable during heat welding. Thus, it should be apparent that the temperature and time required for annealing is a function of the material and is within the scope of one in the art. Further, it should be apparent that the strip of material need not be annealed. Such embodiments are also within the scope of the appended claims.

The strips of material, regardless if they have been annealed, are heat treated to remove toxins. In this process, and for PCL, the strips of material are placed in an oven and heat treated at a temperature of about 55° C. for a period of eight days. It should be apparent that although heat treating the material at the specified temperature for the specific time period, it should be apparent that other temperatures and times are within the scope of the present disclosure. As a non-limiting example, the strips of material may be heated treated at a temperature that is approximately 10% below the melting temperature of the material. Further, the time for the heat treatment may be as little as a few hours. Thus, such times and temperatures are also within the scope of the appended claims.

The heat treated strips of material are also subjected to a sterilization process. In this process, the strips of material are submerged into a sterilization bath of bleach mixture for a sterilization soak period. One bleach mixture is 10% bleach and 90% water. The sterilization soak period ranges substantially between 10 minutes and 40 minutes. In one non-limiting embodiment, the strips of material are soaked in the bleach mixture for a sterilization period of 30 minutes. After the sterilization soak period, the strips of material are subjected to a rinse period in deionized water. The rinse period can last up and beyond 72 hours. Thereafter, the strips of material are air dry in sterile air to evaporate fluids. Finally, the strips of material are processed to make various components of the manufactured seed 20, such as the seed shell 24 and primary end seal 44.

Still referring to FIG. 1, the fill material 120 will now be described in greater detail. Preferably, the fill material 120 is an adsorbent, such as activated charcoal, Dowex resins, zeolites, alumina, clay, diatomaceous earth, silica gel, and Kieselguhr. During assembly of the manufactured seed 20, the fill material 120 is deposited into the cavity 34 of the cylcap 22 in any manner known in the art, including manually. The fill material 120 is preferably, but not necessarily, deposited within the cavity 34 such that it substantially centers the embryo 42 within the cavity 34. Centering the embryo 42 within the cavity 34 increases the surface area of the embryo 42 in functional contact with the nutritive media 26. As used within this detailed description and appended claims, the term "functional contact" is intended to mean in a position where the embryo 42 uptakes nutrients from the nutritive media 26.

The fill material 120 increases the surface area of the embryo 42 in functional contact with the nutritive media 26 by surrounding the embryo 42 and, thereby, providing multiple pathways for the nutrients from the nutritive media 26 to pass to the embryo 42. Although it is preferred that the fill material 120 substantially center the embryo 42 within the cavity 34, the embryo 42 need not be so positioned. The fill material 120 need only position the embryo 42 within the cavity 34 in any manner to place the embryo 42 into functional contact with the nutritive media 26. Further, it is not necessary for the fill material 120 to "surround" the embryo 42. As such, the fill material 120 can completely or partially surround the embryo 42. In other embodiments within the scope of the appended claims, the fill material 120 need only fill, either completely or partially, one or two sides of the space between the embryo 42 and the walls of the cavity 34.

One method of preparing the fill material 120 for insertion into the cavity 34 includes combining approximately 7.0 g of activated charcoal with 246 ml of a nutritive media, such as KE64 media, to create a mixture. One such formulation of the KE64 media is set forth in Table 1.

TABLE 1

| Medium Component | Final Concentration (mg/l) | Amount to add for 300 ml |
|---|---|---|
| NH$_4$NO$_3$ | 301.1 | 2.2 ml |
| H3BO3 | 10.0 | 0.75 ml |
| (NH4)2MoO4 | 0.06 | |
| CaCl2—2H2O | 299.2 | 1.00 ml |
| KH2PO4 | 1800.0 | 7.5 ml |
| MgSO4—7H2O | 1000.0 | |
| MnCl2•4H2O | 6.0 | 0.75 ml |
| ZnSO4—7H2O | 0.8 | |
| CuCl2—2H2O | 0.5 | |
| Ferric Citrate | 60 mg/l | 0.75 ml |

Thereafter, add 30 ml of a 50% sucrose solution and organic stocks are added to the mixture. One such organic stock formulations is set forth in Table 2.

TABLE 2

| Medium Component | Final Concentration mM | Final Concentration (mg/l) | Amount to add for 300 ml complete media |
|---|---|---|---|
| Myo-inositol | 0.5549 | 100.0 | 3.0 ml |
| Thiamine-HCl | 0.0030 | 1.0 | |
| Pyridoxine-HCl | 0.0012 | 0.25 | |
| Nicotinic acid | 0.0081 | 1.0 | |
| Riboflavin | 0.0021 | 0.125 | |
| Ca-pantothenate | | 0.50 | |
| Biotin | 0.0003 | 0.0010 | |
| Folic acid | 0.8077 | 0.1250 | |
| L-asparagine | 1.8255 | 106.7 | 3.0 ml |
| L-glutamine | 0.3646 | 266.7 | |
| L-lysine-2HCl | 0.7612 | 53.3 | |
| DL-serine | 0.4631 | 80 | |
| L-proline | 1.5310 | 53.3 | |
| L-arginine-HCl | 0.4552 | 266.7 | |
| Urea | 13.3200 | 800 | |
| L-valine | 0.5983 | 53.3 | 3.0 ml |
| L-alanine | 0.2203 | 53.3 | |
| L-leucine | 0.2448 | 80 | |
| L-threonine | 0.3226 | 26.7 | |
| L-phenylalanine | 0.1720 | 53.3 | |
| L-histidine | 0.1308 | 26.7 | |
| L-tryptophan | 0.2035 | 26.7 | |
| L-isoleucine | 1.2930 | 26.7 | |
| L-methionine | 0.7100 | 26.7 | |
| L-glycine | 0.0003 | 53.3 | |
| L-tyrosine | 0.2242 | 53.3 | 0.75 ml |
| L-cysteine | 0.6098 | 26.7 | 0.75 ml |

Thereafter, the mixture is autoclaved for about 25 minutes. The mixture is filtered through well-known filter paper and the fill material 120 (e.g., charcoal) is harvested from the filter paper. The harvested fill material 120 is then dried until it becomes flowable matter.

While illustrative embodiments have been illustrated and described, it will be appreciated that various changes can be made therein without departing from the spirit and scope of the invention.

The invention claimed is:

1. A method of manufacturing a manufactured seed, comprising:
    obtaining a seed shell covering having a first end and a second end;
    joining the seed shell covering and a cylcap with at least one heat weld, wherein the cylcap comprises an end seal portion and a cotyledon restraint portion, wherein the end seal portion comprises substantially cylindrical sidewalls, a substantially flat upper surface, and a longitudinal cavity extending from the upper surface through the end seal portion and partially through the cotyledon restraint portion, and wherein the seed shell covering is placed such that an inner portion of the seed shell covering substantially covers the sidewalls of the end seal portion and the first end of the seed shell covering is substantially flush with the upper surface of the end seal portion;
    heating the joined seed shell covering and cylcap such that the seed shell covering and the cylcap bond together;
    filling a space bounded by the seed shell covering, the cylcap, and a dead end seal attached to the second end of the seed shell covering with a nutritive material;
    disposing an embryo and an adsorbent fill material within the longitudinal cavity wherein the fill material substantially fills the portion of the longitudinal cavity outside of the embryo; and bonding a primary end seal to the cylcap via a heat weld and directly connecting the primary end seal to the seed shell via at least one heat weld, and disposing a secondary end seal on at least a portion of the upper surface of the primary end seal.

2. The method of claim 1, wherein the seed shell is formed from strips of biodegradable plastic, the method further comprising:
annealing the strips of biodegradable plastic.

3. The method of claim 2, wherein the annealing comprises exposing the strips of biodegradable plastic to heat at a predetermined temperature for a period of time between about 35 minutes and about 90 minutes.

4. The method of claim 1, wherein the seed shell is formed from strips of biodegradable plastic, the method further comprising:
heat treating the strips of biodegradable plastic.

5. The method of claim 4, wherein the heat treating comprises exposing the strips of biodegradable plastic to heat at a temperature approximately 10% below the melting temperature of the biodegradable plastic for a period of time.

6. The method of claim 4, further comprising:
sterilizing the heat treated strips of biodegradable plastic.

7. The method of claim 6, wherein obtaining the seed shell covering comprises:
forming the heat treated and sterilized strips into the seed shell covering.

8. The method of claim 1, wherein disposing the embryo and the fill material within the longitudinal cavity comprises substantially centering the embryo within the fill material.

9. A method of manufacturing a manufactured seed, comprising:
obtaining a seed shell covering having a first end and a second end;
preheating a cylcap, the cylcap comprising an end seal portion and a cotyledon restraint portion, wherein the end seal portion comprises substantially cylindrical sidewalls, a substantially flat upper surface, and a longitudinal cavity extending from the upper surface through the end seal portion and partially through the cotyledon restraint portion;
placing the seed shell covering on the preheated cylcap such that the seed shell covering and the preheated cylcap bond together, wherein the seed shell covering is placed such that an inner portion of the seed shell covering substantially covers the sidewalls of the end seal portion and the first end of the seed shell covering is substantially flush with the upper surface of the end seal portion;
filling a space bounded by the seed shell covering, the cylcap, and a dead end seal attached to the second end of the seed shell covering with a nutritive material;
disposing an embryo and an adsorbent fill material within the longitudinal cavity wherein the fill material substantially fills the portion of the longitudinal cavity outside of the embryo; and
bonding a primary end seal to the cylcap via a heat weld and directly connecting the primary end seal to the seed shell via at least one heat weld, and disposing a secondary end seal on at least a portion of the upper surface of the primary end seal.

10. The method of claim 9, wherein the seed shell is formed from strips of biodegradable plastic, the method further comprising:
heat treating the strips of biodegradable plastic; and
sterilizing the heat treated strips of biodegradable plastic.

11. The method of claim 10, wherein obtaining the seed shell covering comprises:
forming the heat treated and sterilized strips into the seed shell covering.

12. The method of claim 9, wherein disposing the embryo and the fill material within the longitudinal cavity comprises substantially centering the embryo within the fill material.

13. A manufactured seed, comprising:
a cylcap comprising an end seal portion and a cotyledon restraint portion, the end seal portion having substantially cylindrical sidewalls and a substantially flat upper surface, wherein the cylcap further comprises a longitudinal cavity extending from the upper surface through the end seal portion and partially through the cotyledon restraint portion;
a seed shell covering having a first end and a second end, wherein an inner portion of the seed shell covering is connected to the sidewalls of the end seal portion of the cylcap via at least one heat weld and via at least one melted portion, and wherein the first end of the seed shell covering is located substantially flush with the upper surface of the end seal portion of the cylcap, and;
a dead end seal in contact with and substantially covering the second end of the seed shell covering;
a nutritive material substantially filling the space bounded by the cylcap, the seed shell covering, and the dead end seal;
an adsorbent fill material disposed inside the longitudinal cavity;
an embryo disposed within the fill material, wherein the fill material substantially fills the portion of the longitudinal cavity outside of the embryo; and
a live seal comprising a primary end seal and a secondary end seal, wherein the secondary end seal is disposed on at least a portion of the upper surface of the end seal portion, and wherein the primary end seal is heat welded to the cylcap, and is directly connected to the seed shell via at least one heat weld.

14. The manufactured seed of claim 13, wherein the seed shell is formed from strips of biodegradable plastic.

15. The manufactured seed of claim 14, wherein the strips of biodegradable plastic have been annealed.

16. The manufactured seed of claim 14, wherein the strips of biodegradable plastic have been heat treated to remove toxins.

17. The manufactured seed of claim 16, wherein the heat treated strips of biodegradable plastic have sterilized.

18. The manufactures seed of claim 13, wherein the adsorbent material comprises one or more of activated charcoal, Dowex resins, zeolites, alumina, clay, diatomaceous earth, silica gel, and Kieselguhr.

19. The manufactured seed of claim 13, wherein the embryo is substantially centered within the fill material.

\* \* \* \* \*